United States Patent [19]

Sy

[11] Patent Number: 5,847,251

[45] Date of Patent: Dec. 8, 1998

[54] MULTIBED TRANSALKYLATOR AND PROCESS

[75] Inventor: Angel Sy, Houston, Tex.

[73] Assignee: Catalytic Distillation Technologies, Pasadena, Tex.

[21] Appl. No.: 600,250

[22] Filed: Feb. 12, 1996

[51] Int. Cl.⁶ .............................. C07C 1/00; C07C 15/00
[52] U.S. Cl. ..................... 585/323; 585/310; 585/412; 585/470; 585/920
[58] Field of Search .................................. 585/323, 470, 585/920, 412, 310

[56] References Cited

U.S. PATENT DOCUMENTS

| | | | |
|---|---|---|---|
| 4,317,949 | 3/1982 | Vaughan | 585/458 |
| 4,469,908 | 9/1984 | Burress | 585/467 |
| 4,570,027 | 2/1986 | Boucher | 585/455 |
| 4,849,569 | 7/1989 | Smith, Jr. | 585/466 |
| 4,891,458 | 1/1990 | Innes et al. | 585/323 |
| 4,950,834 | 8/1990 | Arganbright et al. | 585/446 |
| 5,019,669 | 5/1991 | Adams et al. | 585/446 |
| 5,055,627 | 10/1991 | Smith, Jr. et al. | 585/467 |
| 5,081,323 | 1/1992 | Innes et al. | 585/449 |
| 5,086,193 | 2/1992 | Sy | 585/446 |
| 5,113,031 | 5/1992 | Sy | 585/467 |
| 5,215,725 | 6/1993 | Sy | 422/212 |
| 5,243,115 | 9/1993 | Smith, Jr. et al. | 585/446 |
| 5,262,576 | 11/1993 | Smith, Jr. | 585/447 |
| 5,306,852 | 4/1994 | Cosyns et al. | 585/310 |

Primary Examiner—Glenn Caldarola
Assistant Examiner—In Suk Bullock
Attorney, Agent, or Firm—Kenneth H. Johnson

[57] ABSTRACT

A transalkylation reactor having a plurality of catalyst beds with individual feed points for each bed for converting poly alkylated benzene, typically products from a alkylation process, to mono alkylated benzene. Only so many of the catalyst beds are used to optimize the conversion of poly substituted benzene to mono substituted benzene. As the catalyst ages more of the beds are utilized to maintain conversion.

8 Claims, 1 Drawing Sheet

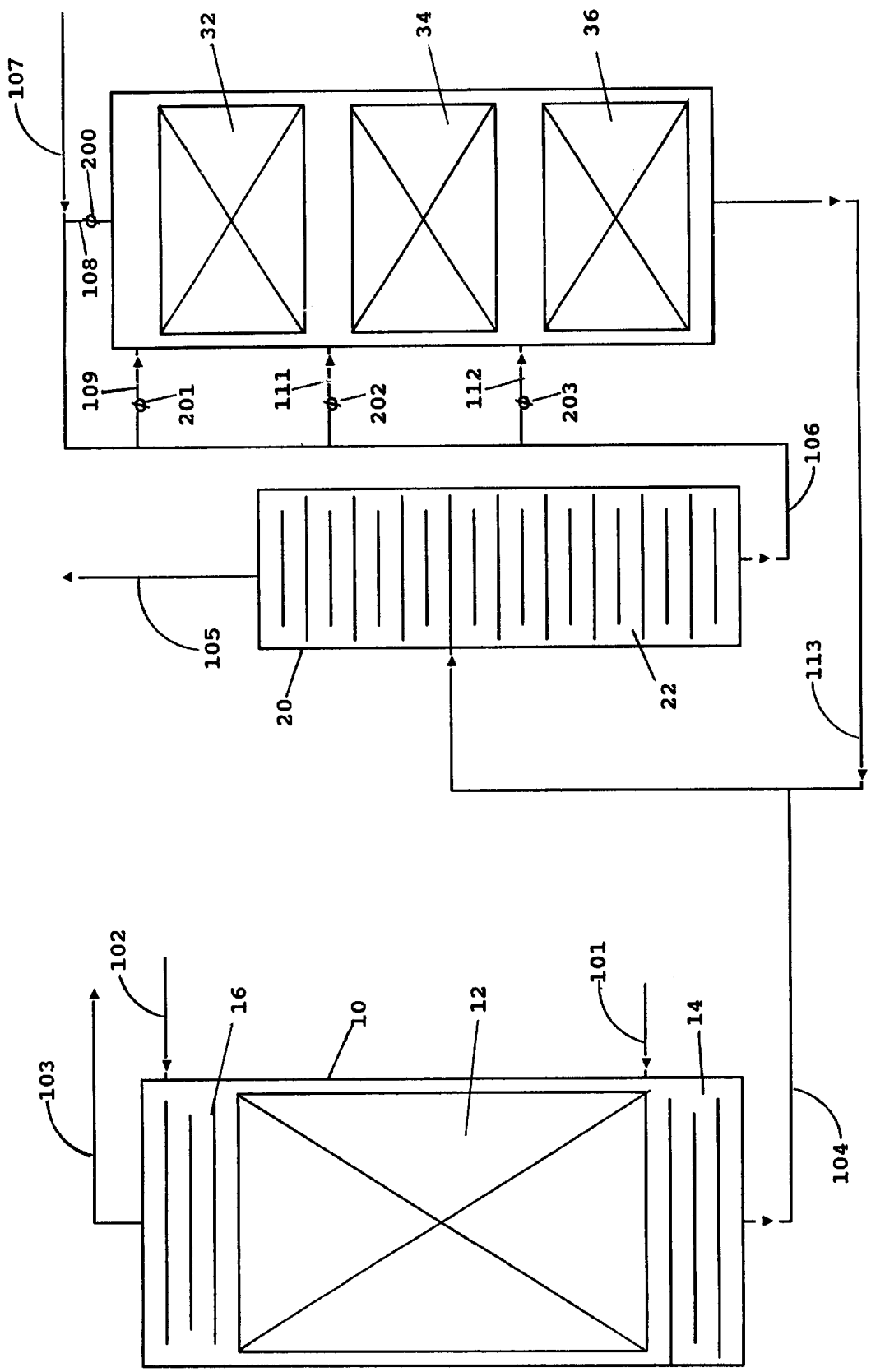

MULTIBED TRANSALKYLATOR AND PROCESS

BACKGROUND OF THE INVENTION

1. Field of the Invention

The present invention relates to a process and apparatus wherein poly substituted benzenes are transalkylated to form additional mono substituted product. More particularly the invention relates to a process for the alkylation of benzene where polyalkylated benzenes are by-products which are transalkylated in a separate apparatus and process step.

2. Related Information

Ethyl benzene and cumene have traditionally been produced by the reaction of benzene and the respective olefin, i.e., ethylene and propylene in the presence of an acidic catalyst. In some known processes the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction tends to produce poly substituted benzene. In the case of ethyl benzene production the poly substituted benzenes are diethyl benzenes. In the case of cumene production the poly substituted benzenes comprise poly isopropyl benzenes (PIPB) which include di-isopropyl benzenes (DIPB's). In addition heavier compounds may also be produced.

The poly substituted benzenes may be transalkylated with additional benzene utilizing the same catalyst as the alkylation catalyst to produce more of the mono substituted benzene. It has been observed that there is an optimum per pass conversion of poly substituted benzene which minimizes impurity formation and results in improved yield and better purity product. The poly substituted benzene conversion is significantly affected by various combinations of temperature and residence time. The various reaction chemistry involved is very complex and is presently not fully understood. Some of the reactions benefit from high temperature and low residence time, and others are affected adversely by too long a residence time. In the past, however, overexposure to excess catalyst could not be avoided, since in most commercial designs, catalyst reserve (excess) was provided to account for catalyst aging so that the desired run length could be attained.

SUMMARY OF THE INVENTION

The present invention comprises providing a transalkylation reactor with multiple beds and feed points so that unneeded catalyst can be by-passed until such time as the aging of the catalyst required the additional catalyst. To prevent contamination of the unused beds by the reactants, the unused beds may be flooded with clean benzene (which is a required reactant in the transalkylation reaction) and a slight flow of the benzene through the unused beds into the active beds maintained.

BRIEF DESCRIPTION OF THE DRAWING

The FIGURE is a flow diagram in schematic form of one process utilizing the invention.

DETAILED DESCRIPTION OF THE PREFERRED EMBODIMENT

Typically the poly substituted benzene mixture is obtained from a primary alkylation of benzene with either ethylene or propylene to produce ethyl benzene or cumene. Many of the disadvantages of the conventional processes have been overcome in a process wherein the reaction of the olefin with benzene is carried out concurrently with separation of the products by fractional distillation. One embodiment of that process is disclosed in U.S. Pat. No. 5,243,115. More particularly the primary alkylation is preferably carried out in a catalytic distillation column reactor as described in commonly assigned U.S. Pat. No. 4,849,569 (ethyl benzene) and U.S. Pat. No. 5,055,627 (cumene) which are hereby incorporated herein by reference. However, the invention can be practiced on a poly substituted benzene mixture from any source.

Thus one embodiment of the invention can be described as An integrated process for the alkylation of organic aromatic compounds, comprising:

(A) contacting a molar excess of benzene with an olefin in a distillation column reactor containing a fixed bed molecular sieve characterized as acidic catalytic distillation structure in a distillation reaction zone, thereby concurrently:

(i) catalytically reacting said benzene and olefin to form alkylation product comprising mono substituted benzene and poly substituted benzene, (ii) withdrawing said alkylation product at a point below said fixed bed, and (iv) withdrawing unreacted benzene at a point above said fixed bed;

(B) fractionating said withdrawn alkylation product;

(C) recovering mono substituted benzene as a product from said fractionation;

(D) recovering poly substituted benzenes as bottoms from said fractionation, (E) feeding said poly substituted benzenes and benzene in liquid phase to a transalkylator containing a plurality of fixed beds of molecular sieve catalyst in series such that only so many of said plurality of beds is used to provide the optimum conversion of the poly substituted benzenes to mono substituted benzene;

(F) recovering a transalkylated product containing mono substituted benzene;

(G) filling the unused bed of said transalkylator with benzene; and (H) maintaining a constant flow of benzene through the unused beds of said transalkylator.

Briefly, the catalytic distillation alkylation is a process for the preparation of alkylated benzene by contacting the benzene with the olefin in a distillation column reactor containing a fixed bed acidic catalytic distillation structure comprising molecular sieve in a distillation reaction zone thereby catalytically reacting said benzene and said olefin (ethylene or propylene) to produce an alkylated benzene product and concurrently in said fixed bed fractionating the resultant alkylated benzene product from the unreacted materials (preferably by fractional distillation). The principal alkylated benzene product is either ethyl benzene or cumene. In addition there are other alkylated products including di and tri isopropyl benzene, n-propyl benzene, ethyl benzene, toluene, diethyl benzene and di-n-propyl benzene, which are believed to be disproportion and isomerization products of cumene.

The ethylene or propylene feed to the reaction is preferably made below the catalyst bed thereby allowing mixing of the reactants before contact with the catalyst bed. In another embodiment the olefin feed to the reaction is preferably made into the catalyst bed thereby allowing immediate contact of this reactant with the benzene in the catalyst to thereby react as much of the two as possible and reduce or eliminate the olefin leaving the reactor as overhead or bottoms, such as between the bottom of the fixed bed, and the upper one-fourth section thereof preferably in the middle one-half of the bed. For example, in the case of alkylation of benzene (B.P. 80° C.) with propylene, the olefin feed may be located below the bed.

The benzene feed may be added at any point in the reactor, however, preferably it is added to the fixed bed or to the reflux as makeup.

Also, in order to achieve high selectivity toward mono substitution (which is a preferred aspect of the present invention), there is a large excess of the organic aromatic compound to the olefin in the reactor in the range of 2 to 100 moles of benzene per mole of olefin, that is, the net molar feed ratio of aromatic organic compound: olefin may be close to 1:1, although the system is operated so as to maintain a substantial molar excess of organic aromatic compound to olefin in the reaction zone. In the event the make up benzene for the transalkylation is to be derived from the overhead/reflux stream of the alkylation reactor the feed molar ratio of the benzene: propylene may exceed 1:1, e.g. 1.1–2:1.

The alkylated product is the highest boiling material and is separated in the lower portion of the column usually as bottoms. The benzene compound is the second highest boiling component (excluding inerts) as noted above, however, by operating with a large excess of benzene in the reactor and a catalytic zone of sufficient height, the major portion of the olefin is reacted, thereby reducing the separation and recovery problems.

The temperature in the distillation column reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa. It can also be appreciated that in catalytic distillation as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

Catalysts which are suitable for both the primary alkylation and the transalkylation reaction are the acidic molecular sieves.

Molecular sieves are porous crystalline, three-dimensional alumina-silicates of the zeolite mineral group. The crystal skeleton is composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e. in so far as the natural zeolites are the functional equivalents to the synthetic zeolites.

Usually synthetic zeolites are prepared in the sodium form, that is, with a sodium cation in close proximity to each aluminum tetrahedron and balancing its charge. To date four principal types of molecular sieves have been reported, A, X, Y and L erionite, omega, beta and mordenite. The A types have relative small pore size. By the term pore size is meant the effective pore size (diameter) rather than the free pore size (diameter). Types X and Y have larger pore size (approximately 10 Å.) and differ as to the range of ratio of $Al_2O_3$ to $SiO_2$ as:

Type X—$Al_2O_3/2.0$–$3.0$ $SiO_2$
Type Y—$Al_2O_3/3.0$–$6.0$ $SiO_2$
Type L, beta and other types listed have still higher ratios of $SiO_2$ to $Al_2O_3$.

The mole sieve catalysts employed in the present invention are the acid form mole sieves or exhibit acidic characteristics. The acid form of the mole sieves is commercially available, but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation leaving the acid form. Generally the Na form mole sieve is treated with soluble ammonium salts to remove the Na and thereafter the mole sieve is heated to a temperature of about 350° C. to remove the ammonia. The removal of $Na^+$ ions with $NH_4^+$ is more easily carried out than with multivalent ions as described below and these catalysts are generally more active, but less stable to heat than the multivalent cation exchange forms. Mole sieves, which have had their alkali metal reduced to low levels by partial treatment with $NH_4^+$ and partial multivalent metal cation exchange, possess increased activity and increased stability.

In addition to mole sieves which are acidic according to the Brönsted Theory, those mole sieves which exhibit acidic characteristics under the Lewis Theory, for example, calcium exchanged mole sieves are suitable for the present reaction. By exchanging the univalent cations (e.g. $Na^+$) with multivalent cation, strong ionic activity is imparted. The ratio of $SiO_2:Al_2O_3$, valence and radius of the cation and the extent of exchange all affect the catalyst activity. In general activity increases with (1) increased $SiO_2:Al_2O_3$ ratio, (2) decreased cation radius and an increase in cation valence. The effect of replacing univalent ions (e.g. $Na^+$) with bivalent (e.g. $Ca^{++}$) is much greater than replacing the bivalent ions with cations of greater valence.

The various types of mole sieves having reduced alkali metal content are characterized as the acid form molecular sieve and are all contemplated as useful in the present invention.

It would appear that the pore size within the crystal lattice may affect selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to site can be altered by altering the structure of the crystal. The acid form mole sieves are generally produced and available as particles in the range of <10 micron (powders) to 0.2 inch in diameter (beads).

In the operation of the transalkylator a sufficient quantity of benzene is required to allow the reaction to proceed. The benzene may be added to the feed to the transalkylator along with the residual from the ethyl benzene or cumene separation. The transalkylation reactor (transalkylator) can be either a standard downflow or upflow single pass fixed bed reactor containing the catalyst. However, there are several distinct beds of catalyst with an inlet near the top (for downflow) or bottom (for upflow) of each bed. Each inlet includes a valve to control the flow to the bed. The poly substituted benzene mixture is passed to the reactor along with excess benzene. In addition, clean benzene is maintained in each of the unused beds by addition at the top (for downflow) or bottom (for upflow) of the reactor.

Typically the conditions within the reactor are between 250° and 520° F. and pressures of between 250 to 600 psig with a liquid hourly space velocity in the range of 0.1 to 10. Benzene is provided in the mole ratio of about 1.5 to 10.0 moles of benzene for each mole of poly substituted benzene.

Referring now to the figure one embodiment for an integrated process for the production of cumene and the transalkylation of PIPB is shown. Benzene and propylene are fed to an alkylation reactor 10 via flow lines 102 and 101 respectively. In the embodiment shown the alkylation reactor is a combined reactor distillation column containing a bed 12 of the catalyst (acidic mole sieve or acidic cation exchange resin) in the form of a catalytic distillation structure. The unreacted benzene is taken as overheads via flow line 103 while the products are taken as bottoms via flow line 104. The reactor products contain cumene and the PIPB.

The bottoms from the alkylation reactor are fed to a cumene distillation column 20 via flow line 104 where cumene is taken overhead via flow line 105 and a PIPB mixture is removed as bottoms via flow line 106. The PIPB mixture in flow line 106 is fed to a header 110 which directs feed to a single pass fixed bed transalkylator 30, operated in a downflow manner and containing a plurality of beds 32, 34 and 36 of catalyst in series (preferably acidic mole sieve). Benzene for the transalkylation reaction is fed via line 107.

Prior to starting the transalkylator the reactor 30 is filled with clean benzene via flow line 108 by opening valve 204 concurrently in this embodiment benzene is also fed to header 110 and mixed with the PIPB feed to the transalkylator 30. During the early part of the run valves 201 and 202 are kept closed and valve 203 is opened allowing feed (PIPB and benzene) to enter bed 36 via flow line 112. A positive flow of benzene is maintained in beds 32 and 34 to prevent backflow into those unused beds. As the catalyst ages in bed 36 and an additional volume of catalyst is required to maintain the desired conversion valve 202 and then 201 are opened to allow flow to beds 34 and 32 respectively through flow lines 111 and 109 respectively.

The effluent from the transalkylator 30 containing cumene and unconverted PIPB is taken via flow line 113 and passed back to join the effluent from the alkylation reactor 10 as feed to the cumene distillation column 20.

An ethyl benzene process would be similar to the cumene process and upflow would be designated by simply inverting the transalkylator.

The invention claimed is:

1. A process for the transalkylation of poly substituted benzene comprising feeding benzene to the topmost of a plurality of vertically serial transalkyalation catalysts beds thereby continuously contacting all of the vertically serial transalkylation beds, feeding poly substituted benzene and benzene to only the lowest bed of a plurality of vertically serial transalkylation catalyst beds under conditions to obtain a first level of mono substituted benzene production, until said first level declines, then additionally feeding said poly substituted benzene and benzene to the next adjacent serial bed transalkylation catalyst such that the effluent from said next bed adjacent passes through said lowest bed.

2. In a process for the alkylation of benzene with an olefin and the subsequent transalkylation of poly substituted products, the improvement comprising providing a transalkylator having a plurality of transalkylation catalyst beds in vertical series and an individual feed entry point for each of said beds such that only so many of said plurality of beds is used in series to provide the optimum conversion of the poly substituted benzenes to mono substituted benzene, said number of bed being increased as the actual conversion decreases, and wherein said unused bed are filled with benzene to prevent poly substituted benzenes from contacting said unused beds.

3. The process according to claim 2 wherein a constant flow of benzene is maintained through said unused beds.

4. An integrated process for the alkylation of organic aromatic compounds, comprising:

(A) contacting a molar excess of benzene with an olefin in a distillation column reactor containing a fixed bed molecular sieve characterized as acidic catalytic distillation structure in a distillation reaction zone, thereby concurrently:

(i) catalytically reacting said benzene and olefin to form alkylation product comprising mono substituted benzene and poly substituted benzene, (ii) withdrawing said alkylation product at a point below said fixed bed, and (iv) withdrawing unreacted benzene at a point above said fixed bed;

(B) fractionating said withdrawn alkylation product;

(C) recovering mono substituted benzene as a product from said fractionation;

(D) recovering poly substituted benzenes as bottoms from said fractionation, (E) feeding said poly substituted benzenes and benzene in liquid phase to a transalkylator containing a plurality of fixed beds of molecular sieve catalyst in series such that only so many of said plurality of beds is used in series to provide the optimum conversion of the poly substituted benzenes to mono substituted benzene, said number of beds being increased as the actual conversion decreases;

(F) recovering a transalkylated product containing mono substituted benzene; and (G) filling the unused bed of said transalkylator with benzene.

5. The process according to claim 4 wherein said olefin is ethylene and said mono substituted benzene is ethyl benzene.

6. The process according to claim 4 wherein said olefin is propylene and said mono substituted benzene is cumene.

7. The process according to claim 6 wherein a constant flow of benzene is maintained through said unused beds.

8. The process according to claim 4 further comprising:

(H) maintaining a constant flow of benzene through the unused beds said transalkylator.

* * * * *